United States Patent

Wojciechowicz et al.

[11] Patent Number: 5,830,234
[45] Date of Patent: Nov. 3, 1998

[54] METHOD FOR DOUBLE WIRE STERNOTOMY SUTURE

[75] Inventors: Alex F. Wojciechowicz, Princeton, N.J.; Garth R. McDonald, Phoenix, Md.

[73] Assignee: Alto Development Corporation, Farmingdale, N.J.

[21] Appl. No.: 884,302

[22] Filed: Jun. 27, 1997

Related U.S. Application Data

[60] Provisional application No. 60/042,650 Apr. 4, 1997.

[51] Int. Cl.$^6$ ..................................................... A61B 17/00
[52] U.S. Cl. ........................................... 606/224; 606/226
[58] Field of Search ..................................... 606/224, 225, 606/226, 227, 228, 232

[56] References Cited

U.S. PATENT DOCUMENTS

| | | |
|---|---|---|
| 3,762,418 | 10/1973 | Wasson . |
| 4,201,215 | 5/1980 | Crossett et al. . |
| 4,512,346 | 4/1985 | Lemole . |
| 4,535,764 | 8/1985 | Ebert . |
| 4,602,636 | 7/1986 | Noiles . |
| 4,813,416 | 3/1989 | Pollak et al. . |
| 4,901,721 | 2/1990 | Hakki . |
| 5,089,012 | 2/1992 | Prou . |
| 5,092,868 | 3/1992 | Mehdian . |
| 5,259,846 | 11/1993 | Granger et al. . |
| 5,501,688 | 3/1996 | Whiteside et al. . |

*Primary Examiner*—Michael Powell Buiz
*Assistant Examiner*—Vikki Trinh
*Attorney, Agent, or Firm*—Woodbridge & Associates

[57] ABSTRACT

A sternotomy suture comprises a loop which passes around a split sternum and is twisted until double cabling begins at which point the suture is fastened to itself. The loop preferably comprises a single strand of wire with one end welded to an intermediate point of said strand leaving a portion available for connection to the needle. A curved needle having a cutting tapered point is swaged to the free end of the single strand. Initially the wire is passed around the split sternum and the needle then removed with a pair of diagonal cutting pliers. A twisting tool, having a handle and a hooked portion, passes through the two free loops on opposite sides of the sternum. Twisting force is applied to the tool and transmitted through the hook to the suture causing it to twist and cable. The suture reaches its critical length $L_{crit}$ when the loop is fully cabled but before double cabling begins. At the onset of double cabling the loop reaches its maximum tension $T_{crit}$. This is the signal to the surgeon to stop turning and to fasten the loop to itself. As a consequence, the resulting sternotomy suture is applied with optimal force. The loop is not too tight to cause discomfort and possible complications; nor is the loop too loose thereby creating an inferior bond.

1 Claim, 3 Drawing Sheets

METHOD FOR DOUBLE WIRE STERNOTOMY SUTURE

CROSS-REFERENCE TO RELATED APPLICATIONS

This application is related to, and claims the priority of, our provisional patent application entitled DOUBLE WIRE STERNOTOMY SUTURE filed on Apr. 4, 1997 and issued Provisional patent application Ser. No. 60/042,650, the entire contents of which are hereby incorporated by reference.

BACKGROUND OF THE INVENTION

1. Field of the Invention

The invention relates to a double wire sternotomy suture apparatus and method for closing a split sternum employing optimal force in the process.

2. Description of Related Art

Sternotomy sutures are stainless steel sutures used to lace up the sternum after a surgery that requires cutting the length of the sternum to gain access to the chest cavity. A sternotomy is routinely performed when heart surgery is required. Sternotomy sutures are available from a number of companies such as the MYO/WIRE® suture available from A & E Medical Corporation, 5206 Asbury Road, Farmingdale, N.J. 07727.

In general, history has shown that sternotomy wires are the most safe and effective method for closing the sternum during the period of time necessary for the sternum halves to heal together. The wires are usually left implanted for life because they are atraumatic and removal could cause difficulties especially if bone has grown around the wire. Surgeons prefer the use of wires because they are simple to apply, produce the least post surgical complications, and are relatively inexpensive. The prior art methods, however, have presented some installation and post operative problems described below.

The first major problem is that band tightening by twisting wires together with a pair of pliers is an inexact method. The surgeon has to develop a very sensitive "feel" for how much torque he or she can apply to properly tighten the band without breaking the wire. Consequently, it is common for a great number of suture wires to break during installation. As a counter to this, new wires have been developed which are more resistant to breaking during band tightening. A wire break, however, generally requires the surgeon to undo all finished sutures and start the process all over again. For fear of breaking a wire, a surgeon will tend to under torque the suture resulting in less than optimal closure pressure on the sternal knit line. This can lead to dehiscence problems.

A second major prior art problem relates to the consequence of movement along the sternum knit line. For a number of reasons, many patients develop a chronic cough after surgery that places a heavy stress on the suture wire bands. Stress is even greater for heavy, large chested persons. This can cause the bands to loosen or break. The resulting dehiscence (movement along the sternum knit line) is very bad especially if infection sets in. This condition usually requires a completely new operation to replace and tighten new sternal suture wires along with aggressive antibody treatment for the resulting infection. A reasonable estimate is that dehiscence and/or sternal infection complications incur in 1.5 to 2.0% of all heart surgery patients. Hospitals estimate that the additional cost to treat each of these patients averages $20,000 per patient or $300,000 minimum cumulative cost to a hospital performing 1,000 heart operations a year. Hence, an improvement in sternal closure that reduces dehiscence could be very cost effective and desirable.

The prior art patent literature discloses a handful of loop type surgical devices for other purposes. Note, for example, U.S. Pat. No. 5,259,846 entitled LOOP THREADED COMBINED SURGICAL NEEDLE-SUTURE DEVICE. That disclosure describes incorporating two ends of a looped suture into a surgical needle to facilitate quick knotting and tying as may be needed during critical surgical procedures.

U.S. Pat. No. 3,762,418 entitled SURGICAL SUTURE discloses a double strand, but not looped, suture preferably having needles at both ends. This enables double suturing simultaneously in a single procedure.

U.S. Pat. No. 5,089,012 entitled SURGICAL SUTURE, IN PARTICULAR FOR STERNOTOMY CLOSURE, discloses a typical prior art single needle surgical suture incorporating a single monofilament portion.

U.S. Pat. No. 4,602,636 entitled SUTURE WIRE WITH INTEGRAL NEEDLE-LIKE TIP is of possible relevance for its teaching of a suture having an integrated needle tip therein attached to a single homogenous piece of wire.

U.S. Pat. No. 5,092,868 entitled APPARATUS FOR USE IN THE TREATMENT OF SPINAL DISORDERS teaches an endless loop of wire flattened to form two strands which are employed along with a T-shaped handle to attach a bracket to the spinal cord. It is noted, with interest, however, that the two portions of the strands are mechanically held next to each other and can be manipulated as a unit to guide it through a spinal opening.

U.S. Pat. No. 5,501,688 entitled SURGICAL DEVICE FOR MANIPULATING WIRE discloses a tool and method for tightening a single strand suture having loops at both ends.

Lastly, the following patents are all cited as describing the general state of the art and appear to be of lesser relevance to the disclosed invention: U.S. Pat. Nos. 4,201,215; 4,512, 346; 4,535,764; 4,813,416; and, 4,901,721.

Insofar as understood, none of the disclosed prior art appears to teach, hint or suggest a loop suture suitable for enclosing a split sternum such that optimal force is applied. Moreover, none of the prior art appears to disclose a method and procedure for fastening a suture to itself at the optimal tension $T_{crit}$ when double cabling begins.

It was in the context of the foregoing that the present invention arose.

SUMMARY OF THE INVENTION

Briefly described, the invention comprises a sternotomy suture in the form of a loop which can be employed to close a split sternum with optimal retaining force. The loop is preferably formed from a single strand of wire in which one free end is welded an inch or two below the other free end to form a loop. A standard sternotomy needle having a curved, tapered end is swaged to the remaining free end of the strand.

The procedure comprises the following steps. First, the needle is passed around the split sternum so that a portion of the loop appears on both sides. Second, the free end of the needle is snipped off between the weld and the needle leaving only the loop intact. Third, a twisting tool having a handle and a hooked portion passes through the two open portions of the loop on opposite sides of the sternum. Fourth, the tool is rotated until the loop has been fully absorbed in a single cable at $L_{crit}$. Fifth, continued twisting of the tool causes the suture to begin double cabling. This occurs at the optimal tension $T_{crit}$. At this point the surgeon fastens the loop to itself and snips off the remaining portions. The force applied to the split sternum is optimal and sufficient to close the gap, yet not too tight to cause problems.

These and other features of the apparatus and procedural method may be more fully understood by reference to the following drawings.

DETAILED DESCRIPTION OF THE INVENTION

During the course of this description like numbers will be used to identify like elements according to the different figures which illustrate the invention.

Figure 1:
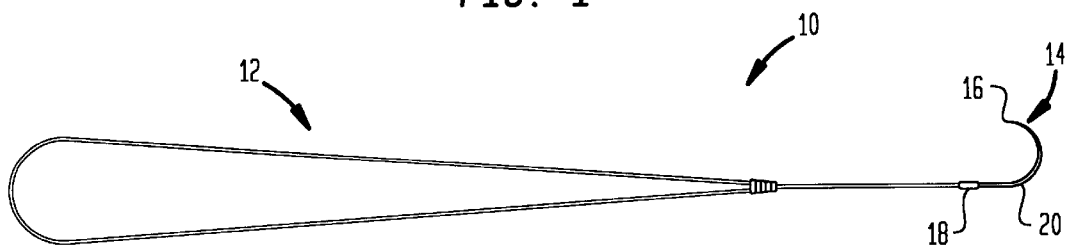
FIG. 1 illustrates the preferred embodiment of the double wire sternotomy suture showing the needle attached to the loop portion of the suture.

The preferred embodiment 10 of the invention is illustrated in FIG. 1. The basic elements of the invention 10 are a loop section 12 and a needle section 14.

Figure 2:
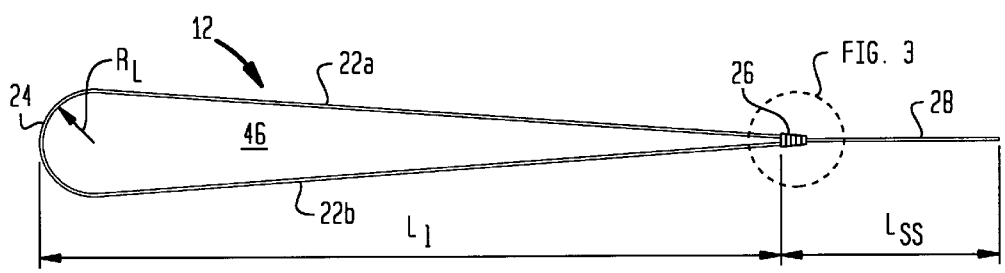
FIG. 2 illustrates just the loop portion, formed from a single piece of wire, welded to itself prior to attachment of the needle section.
Figure 3:
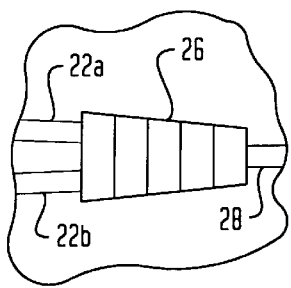
FIG. 3 is a detailed view of the welded portion of the loop suture illustrated in FIG. 2.

The needle section 14 preferably comprises a channel needle having a tip 16, a curved midportion 20, and a base 18 that is swaged to the free end of the strand 28 as illustrated in FIGS. 2 and 3.

The loop portion 12, illustrated in FIGS. 2 and 3, is preferably formed from a single strand of stainless steel suture wire USP#6 or #8 as required. The single strand is doubled back onto itself such that one free end is welded to an intermediate portion of the strand at weld location 26. This results in a loop suture having a first leg 22a, a rounded end section 24, having a radius $R_l$ and a second return leg 22b. The length of the loop portion $L_l$ from the weld section 26 to the curved end 24 is preferably about 11.86 inches. The remaining strand 28 has a length of $L_{ss}$ of roughly 2.00 inches. The strand of stainless suture wire prior to its forming as shown in FIG. 2 is approximately 22 inches in length. The radius $R_l$ of the curved end 24 is preferably about 0.25 inches. The space between legs 22a and 22b form an opening 46.

The weld section 26 of the loop 12 is shown in detail in FIG. 3. The weld 26 is preferably formed of stainless steel welding material and swaged to a tapered shape as shown in order for a smooth transition from the needle section 12 to the loop section.

Figure 4:
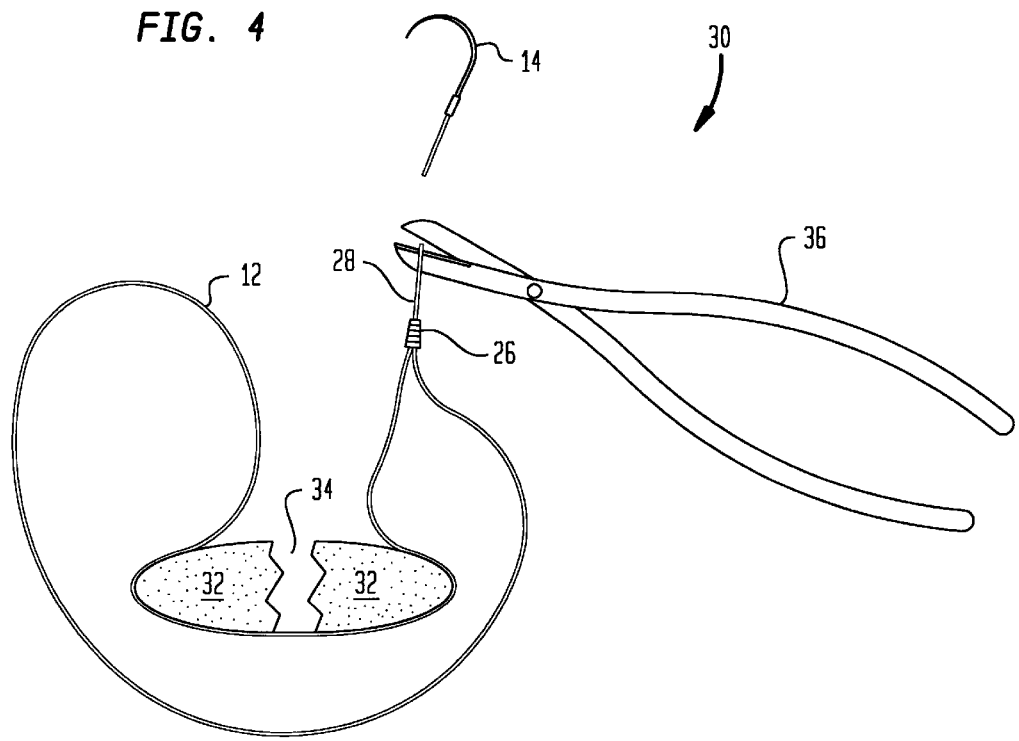
FIG. 4 illustrates the first two steps of the method according to the preferred embodiment of the invention in which the surgical needle has been passed around the split sternum and is subsequently cut off by a pair of diagonal pliers.

The preferred procedural method steps of the invention 10 are illustrated sequentially in FIGS. 4–9. As shown in FIG. 4, the first step 30 of the procedure is to pass the needle 14, in a conventional manner, around the sternum 32 between the intercoastal spaces. The sternum 32 is shown having a split or gap 34 therein which needs to be closed in a safe manner.

The second step of the procedure, also shown in FIG. 4, and identified as element 30, is to cut the needle strand 28 between the weldment 26 and the needle 14 so as to separate the needle 14 from the rest of the loop 12. A pair of diagonal cutting pliers 36, or similar tool, are used to snip the needle 14 from strand 28.

Figure 5:
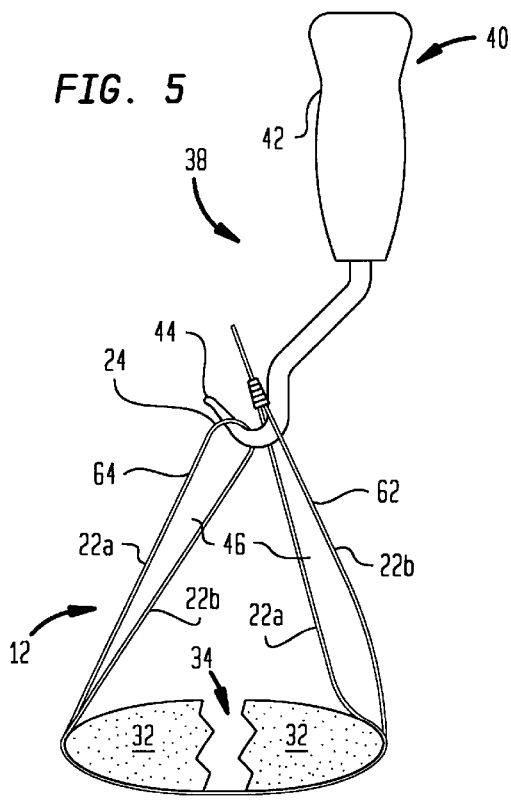
FIG. 5 illustrates the next step of the procedural method in which the hook portion of a twisting tool is passed through the two open portions of the suture loop.

In a third step 38, illustrated in FIG. 5, a twisting tool 40 is employed to twist the two free loop ends 62, 64 together. After the needle 12 has been removed, as illustrated in the first and second step 30 of FIG. 4, the two wires 22a and 22b at the weldment 26 are spread apart to form a first loop section 62 with a gap therein 46. A second loop section 64 is formed naturally on the opposite side from the curved, rounded end 24 and also includes a gap 46 therein. Twisting tool 40 includes a handle section 42 and a hook section 44. The hook section 44 is passed through the gap 46 in the first loop 62 and then through the other gap 46 in the second loop 64 so that both loops 62 and 64 are engaged as shown in FIG. 5.

Figure 6:
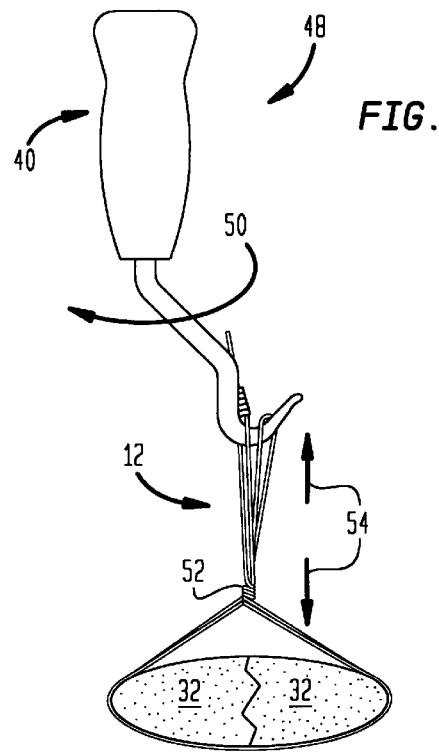
FIG. 6 illustrates the next step of the procedural method in which the twisting tool is turned to cause the surgical loop to begin cabling.

The next, or fourth, step 48 in the procedural method, is illustrated in FIG. 6. The tool 40 is rotated in the direction of arrow 50 causing the loop section 12 to twist or cable in area 52 and exert upward and downward forces as illustrated by arrows 54. Twisting tool 40 continues to rotate in the direction of arrow 50 to twist all four wires (22a, 22b) until the band 12 around the sternum 32 becomes tight and the gap 34 disappears.

Figure 7:
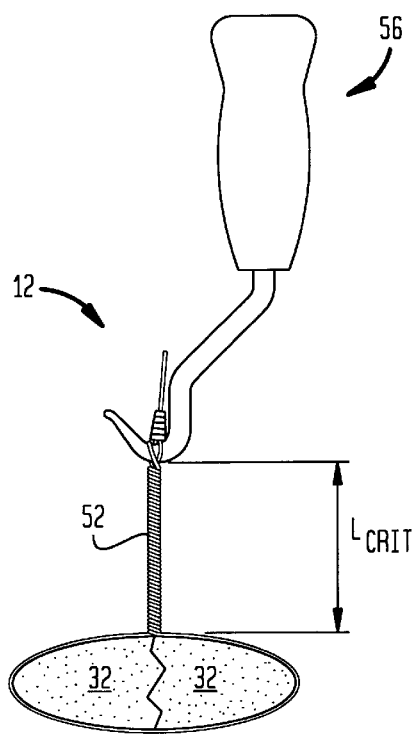
FIG. 7 illustrates the next step of the procedural method in which the loop suture is fully cabled at $L_{crit}$.

The next, or fifth, step 56 in the preferred procedural method is illustrated in FIG. 7. The cabling 52 continues until the loop 12 is fully cabled at a certain critical length referred to as $L_{crit}$. An interesting phenomenon has been observed at this point. It has been noted, for both single and double suture wires, that as the wires are twisted, cabling 52 of the wires starts at a random location, then simultaneously progresses towards the twisting tool 40 at one end and down towards the sternum 32 at the other in the direction of double arrow 54. During this process nearly all of the twisting torque T goes into the cabling effect 52 and not into the tightening of the band 12 around the sternum 32. As the cabling 52, however, fills the space between the twisting tool 40 and the sternum 32, the band loop 12 closes and then begins to tighten when the cabling 52 comes into contact with the sternum 32. It is the rotation of the cable bundle 52 adjacent to the sternum 32 that tightens the band. The forces within the cable bundle 52 are somewhat complex due to the cable construction. In general terms, however, it is the maximum shearing stress within this last cable bundle 52, closest to the sternum 32, that dictates how much the band can tighten before the wire in the loop 12 breaks at the cable knot 52. Elastic theory suggests that the maximum shear stress is proportional to the inverse of the cable diameter cubed. Hence, for a given torque T the maximum shear stress reduces dramatically as the diameter of the cabling 52 increases. The cable diameter of a double wire twist is about twice that for a single wire twist. Accordingly, for a given torque the shear stresses for a double wire are $(½)^3$ or $⅛^{th}$ of those for a single wire. What this implies for a surgeon is that a double wire can be torqued to a band loading much more than double that of a single wire, perhaps as much as 8 times higher.

Figure 8:
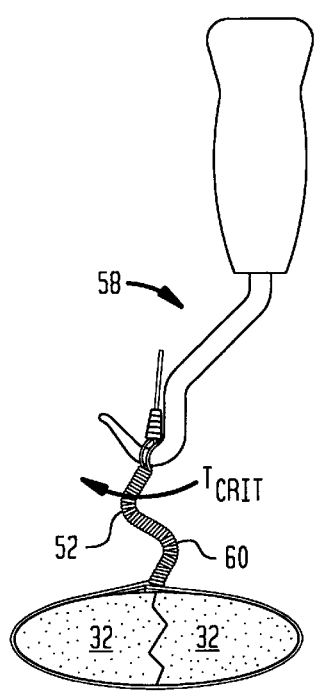
FIG. 8 illustrates the next step of the procedural method in which the loop suture begins to double cable at which point it is cut and fastened at the optimal tension $T_{crit}$.

Accordingly, what is desired is a form of torque limiting to prevent injury to the sternum 32. In particular, it would be desirable to allow a surgeon to install a double wire, such as loop 12, without fear of breaking the wire or causing injury to the patient. One approach might be, for example, to build in some form of weakness into the suture that would cause the cabling to break at a predetermined location and torque value. During experimentation, however, it was observed that once the length of the cable between the twisting tool 40 and the sternum 32 exceeded a certain critical length $L_{crit}$, the cable 12 could only be twisted by a limited amount of torque $T_{crit}$ before the cable 12 starts to twist around itself and form a double cable 60. This comprises the sixth step 58 in the process as illustrated in FIG. 8. It has been further determined that the size of wires most advantageous for sternotomy sutures are USP#5 through USP#8. This $T_{crit}$ produces adequate band tension without fear of breaking the wires 22a, 22b or injuring the patient. It has been found that the optimal wire length required to guarantee a cable length greater than $L_{crit}$ is one that gives a cable length greater than 2 inches for the largest patient. Therefore, employing the preferred procedural method of the present invention, all the surgeon has to do is twist the double suture 12 until it starts to produce double cabling 60 as shown in FIG. 8.

Figure 9:
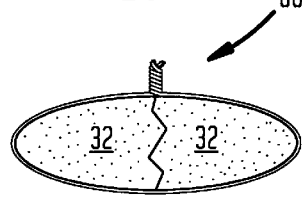
FIG. 9 illustrates the last step of the procedure with the surplus wire cut off.

The cable is then trimmed to a short length as per standard surgical techniques as shown in the last step 66 in FIG. 9.

It is also been determined that the double cabling effect will also occur with single wires. In such a case, the surgeon twists the wire until it starts to double cable. However, because of the lack of torsional rigidity, the band tension is inadequate at that point. Accordingly, the surgeon has to cut the cable short and then apply additional torque T to tighten the band. Therefore, at that time, the surgeon has to use critical judgment to determine when the band is tight enough without breaking the band. It has, therefore, been determined, that double wires, such as loop 12 avoids this additional step and is much more reliable.

Figure 10:
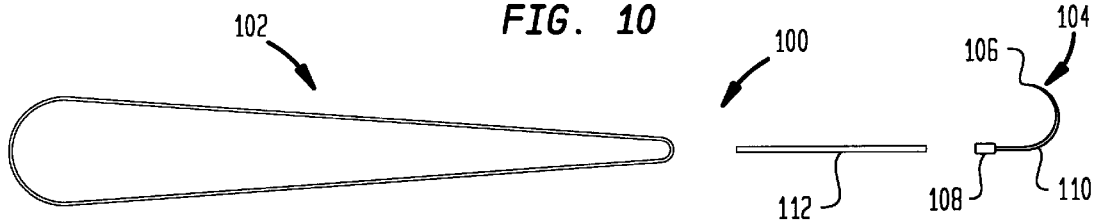
FIG. 10 illustrates an alternative embodiment of the invention in which the double suture is a continuous loop which is connected to a separate leader portion having a different diameter.

The alternative embodiment 100 of the invention is illustrated in FIG. 10. The invention, according to alternative embodiment 100 comprises a continuous loop 102, a separate leader section 112 and a curved needle 104. Curved needle 104 includes a tip 106, a midsection 110 and a butt section 108. The butt section 108 of needle 104 is swaged to the leader section 112 in the same manner that needle 14 is attached to section 28 of the preferred embodiment 10. The leader section 112 of alternative embodiment 100 is welded to continuous loop section 102. The advantages of alternative embodiment 100 is that the diameter of the wire in the continuous loop section 102 can be different from the diameter of the wire in the leader section 112 so that the diameter of the leader section 112 better matches the diameter of the butt section 108 of needle 104. This permits the leader section 112 to be stronger than the wire in the loop section 102. When leader section 112 is welded to loop section 102 the attachment point is taped down so that the transition is relatively smooth and friction free during use.

Figure 11:
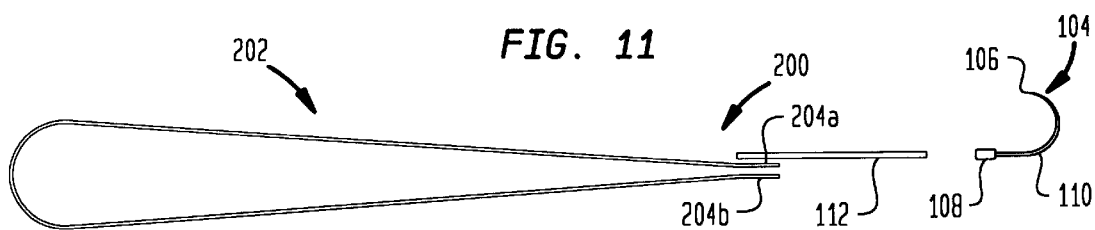
FIG. 11 illustrates another alternative embodiment of the invention in which the double suture is in the form of a loop in which the two free ends of a single continuous piece of suture wire overlap and abut with a separate leader portion having a different, larger diameter and where the three segments are welded to each other in that relationship.

In a second, alternative embodiment 200 illustrated in FIG. 11, the continuous loop 202 is formed from a single strand of suture wire, preferably about 24 inches long, in which the two free ends 204a and 204b are parallel to and abut each other. The separate leader strand 112 also overlaps and abuts with ends 204a and 204b. The three wires 112, 204a and 204b are welded together in an overlapping fashion. This arrangement permits a somewhat larger leader wire 112 to be welded to a somewhat smaller diameter wire 202. Therefore, it is possible to produce a double wire suture 200 having a needle 104 and a leader 112 that are larger in diameter and, therefore, stronger than the double suture portion 202. Accordingly, different size needles 104 can be attached to sutures 202 having different diameter sizes.

In summary, the foregoing double wire sternotomy suture apparatus and procedural method have several advantages over the prior art. First, the method is relatively simple and reliable. As a result, the surgeon does not have to repeat the procedure as often as was required in the prior art due to wire breakage. Second, the pressure applied to the sternum is optimal and predictable. The pressure placed on the sternum is sufficient to close the gap without crushing the intersection. Third, dehiscence, i.e., movement along the sternum knit line, is minimized. As a result, it is estimated that the incidence of dehiscence and/or sternal infection should drop substantially thereby reducing patient morbidity and hospital costs.

While the invention has been described with reference to the preferred embodiment of the sternotomy suture apparatus and its related preferred method of implementation, it will be appreciate by those of ordinary skill in the art that modifications can be made to the structure and steps of the invention without departing from the spirit and scope thereof.

we claim:

1. A method of suturing a split sternum having a gap therein employing a suture in a form of a loop and a needle attached to said suture, said method comprising steps of:

a. passing said needle and at least a portion of said loop around said sternum;

b. cutting off said needle;

c. attaching a tool through said loop, wherein said tool passes through at least two loop portions of said loop;

d. twisting said tool and said loop portions until double cabling begins which corresponds to a constant force applied to said sternum;

e. fastening said loop, wherein said loop tightly closes said gap in said sternum.

* * * * *